(12) United States Patent
Choi et al.

(10) Patent No.: US 11,293,911 B2
(45) Date of Patent: Apr. 5, 2022

(54) MULTI-PHASE LIQUID COMPOSITION, DEVICE FOR MEASURING PERMEABILITY OF DRUGS, AND METHOD FOR MEASURING PERMEABILITY OF DRUGS

(71) Applicant: KOREA ADVANCED INSTITUTE OF SCIENCE AND TECHNOLOGY, Daejeon (KR)

(72) Inventors: Siyoung Choi, Daejeon (KR); Yohan Lee, Daejeon (KR)

(73) Assignee: KOREA ADVANCED INSTITUTE OF SCIENCE AND TECHNOLOGY, Daejeon (KR)

(*) Notice: Subject to any disclaimer, the term of this patent is extended or adjusted under 35 U.S.C. 154(b) by 223 days.

(21) Appl. No.: 16/229,006

(22) Filed: Dec. 21, 2018

(65) Prior Publication Data
US 2019/0204285 A1  Jul. 4, 2019

(30) Foreign Application Priority Data

Dec. 28, 2017 (KR) .................. 10-2017-0182395
Dec. 5, 2018 (KR) .................. 10-2018-0155497

(51) Int. Cl.
| G01N 33/15 | (2006.01) |
| G01N 33/50 | (2006.01) |
| A61K 47/34 | (2017.01) |
| A61K 47/06 | (2006.01) |
| G01N 15/08 | (2006.01) |
| G01N 13/00 | (2006.01) |

(52) U.S. Cl.
CPC ............ *G01N 33/15* (2013.01); *A61K 47/06* (2013.01); *A61K 47/34* (2013.01); *G01N 13/00* (2013.01); *G01N 15/0826* (2013.01); *G01N 33/5008* (2013.01); *G01N 2013/003* (2013.01); *G01N 2015/086* (2013.01)

(58) Field of Classification Search
None
See application file for complete search history.

(56) References Cited

U.S. PATENT DOCUMENTS

| 7,022,528 B2 | 4/2006 | Avdeef et al. |
| 8,986,781 B2 | 3/2015 | Chen et al. |
| 2009/0074988 A1 | 3/2009 | Faris et al. |

(Continued)

FOREIGN PATENT DOCUMENTS

| JP | 3954847 | 8/2007 |
| JP | 2013-500858 | 1/2013 |
| KR | 10-1568565 | 11/2015 |

(Continued)

OTHER PUBLICATIONS

Villar, G. et al. Functional Droplet Interface Bilayers, Encyclopedia of Biophysics, 861-868 (Year: 2013).*

(Continued)

*Primary Examiner* — Xiaoyun R Xu
(74) *Attorney, Agent, or Firm* — Lex IP Meister, PLLC

(57) ABSTRACT

The present invention relates to a multi-phase liquid composition including: a first aqueous phase; a second aqueous phase; a lipid bilayer; and an organic phase, a device for measuring the permeability of drugs including the multi-phase liquid composition, and a method for measuring the permeability of drugs.

19 Claims, 4 Drawing Sheets

(56) References Cited

U.S. PATENT DOCUMENTS

2015/0285781 A1   10/2015   Heron et al.

FOREIGN PATENT DOCUMENTS

| KR | 10-1586036 | 1/2016 |
|---|---|---|
| WO | 2015/177811 | 11/2015 |

OTHER PUBLICATIONS

T. Hauβ et al., "Squalane is in the midplane of the lipid bilayer: implications for its function as a proton permeability barrier", Biochimica et Biophysica Acta, 2002, pp. 149-154, vol. 1556.

D.-W. Jeong et al., "Enhanced stability of freestanding lipid bilayer and its stability criteria", Scientific Reports, 2016, vol. 6, No. 38158.

S. Leptihn et al., "Constructing droplet interface bilayers from the contact of aqueous droplets in oil", nature protocols, 2013, vol. 8, No. 6.

H. Bayley et al., "Droplet interface bilayers", Molecular BioSystems, 2008, pp. 1191-1208, vol. 4, No. 12.

G. de Wit et al., "Dynamic label-free imaging of lipid nanodomains", PNAS, vol. 112, No. 40, 2005, pp. 12299-12303.

T. Nisisako et al., "Microfluidic passive permeability assay using nanoliter droplet interface lipid bilayers", Analyst, vol. 138, 2013, pp. 6793-6800.

V. A. Parsegian et al., "A comment on models of ion transport across cell membranes", Annals of Biomedical Engineering, vol. 3, 1975, pp. 433-438.

M. H. Saier et al., "A functional-phylogenetic classification system for transmembrane solute transporters", Microbiology and Molecular Biology Reviews, vol. 64, No. 2, 2000, pp. 354-411.

P. D. Dobson et al., "Carrier-mediated cellular uptake of pharmaceutical drugs: an exception or the rule?", Nature Reviews, Drug Discovery, vol. 7, pp. 205-220, 2008.

The International Transporter Consortium, "Membrane transporters in drug development", Nature Reviews, Drug Discovery, vol. 9, pp. 215-236, 2010.

K. Sugano et al., "Coexistence of passive and carrier-mediated processes in drug transport", Nature Reviews, Drug Discovery, vol. 9, pp. 597-614, 2010.

J. H. Yeon et al., "Drug permeability assay using microhole-trapped cells in a microfluidic device", Analytical Chemistry, vol. 81, No. 5, pp. 1944-1951, 2009.

H. Bohets et al., "Strategies for absorption screening in drug discovery and development", Current Topics in Medicinal Chemistry, vol. 1, pp. 367-383, 2001.

P. V. Balimane et al., "Current industrial practices of assessing permeability and P-Glycoprotein interaction", The AAPS Journal, vol. 8, No. 1, article 1, pp. E1-E13, 2006.

P. Artursson et al., "Intestinal drug absorption and metabolism in cell cultures: Caco-2 and beyond", Pharmaceutical Research, vol. 14, No. 12, pp. 1655-1658, 1997.

P. V. Balimane et al., "A critique of cell culture models for intestinal permeability", Drug Discovery Today, vol. 10, No. 5, pp. 335-343, 2005.

A. M. Marino et al., "Validation of the 96 well Caco-2 cell culture model for high throughput permeability assessment of discovery compounds" International Journal of Pharmaceutics, vol. 297, pp. 235-241, 2005.

A.-L. B. Ungell, "Caco-2 replace or refine?", Drug Discovery Today: Technologies, vol. 1, No. 4, pp. 423-430, 2004.

H. Sun et al., "Response to Letter to the Editor on 'Permeability, Transport, and Metabolism of Solutes in Caco-2 Cell Monolayers: A Theoretical Study'", Drug Metabolism and Disposition, vol. 38, No. 3, pp. 536-537, 2010.

M. Kansy et al., "Physicochemical high throughput screening: Parallel artificial membrane permeation assay in the description of passive absorption processes", Journal of Medicinal Chemistry, vol. 41, No. 7, pp. 1007-1010, 1998.

C. Zhu et al., "A comparative study of artificial memerane permeability assay for high throughput profiling of drug absorption potential", European Journal of Medicinal Chemistry, vol. 37, pp. 399-407, 2002.

A. Avdeef et al., "Drug absorption in vitro model: filter-immobilized artificial membranes", European Journal of Pharmaceutical Sciences, vol. 14, pp. 271-280, 2001.

F. Wohnsland et al., "High-throughput permeability pH profile and high-throughput alkane/water log P with artificial membranes", Journal of Medicinal Chemistry, vol. 44, pp. 923-930, 2001.

K. Sugano et al., "Prediction of passive intestinal absorption using bio-mimetic artificial membrane permeation assay and the paracellular pathway model", International Journal of Pharmaceutics, vol. 241, pp. 241-251, 2002.

X. Chen et al., "A Novel Design of artificial membrane for improving the PAMPA model", Pharmaceutical Research, vol. 25, No. 7, pp. 1511-1520, 2008.

A. Avdeef, "Absorption and Drug Development: Solubility, Permeability, and Charge State", 2nd edition, Wiley: New York, pp. 139-147, 2012.

\* cited by examiner

[FIG. 1]
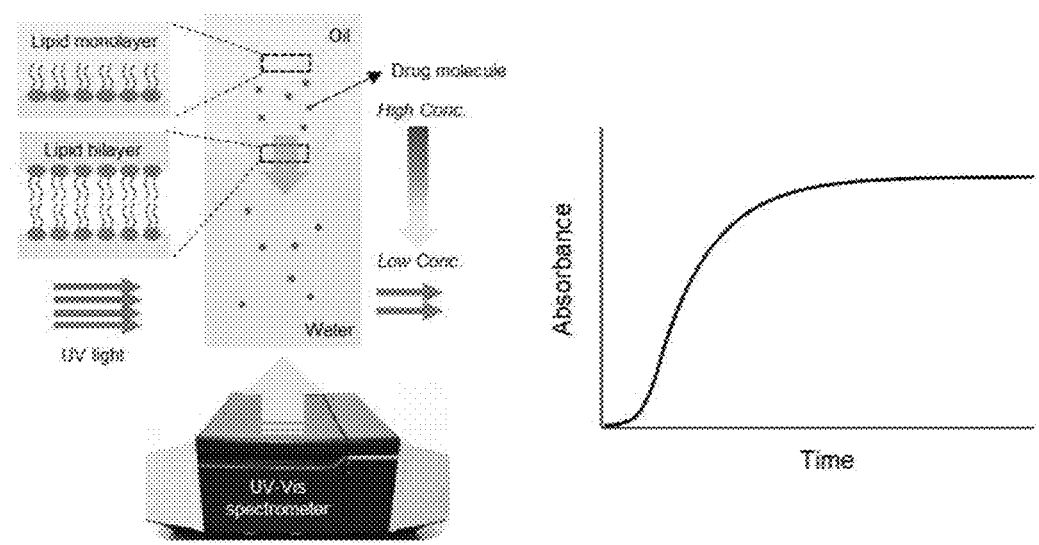

[FIG. 2]
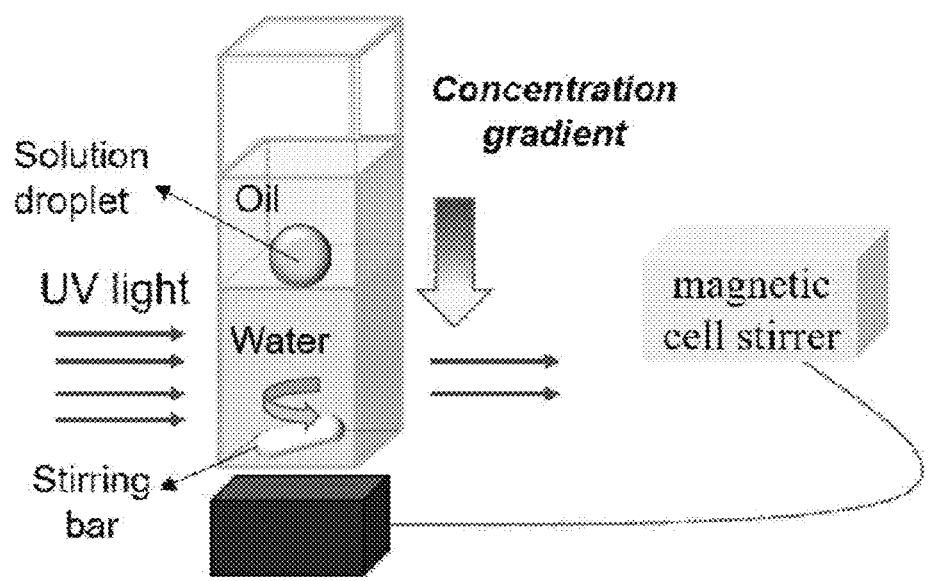

[FIG. 3]
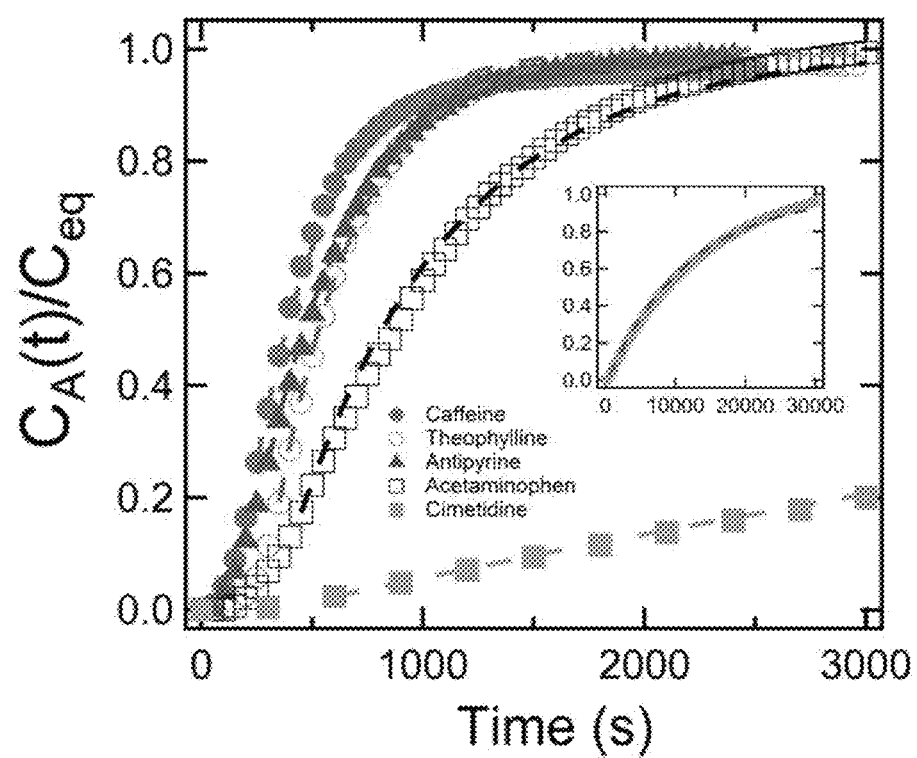

[FIG. 4]
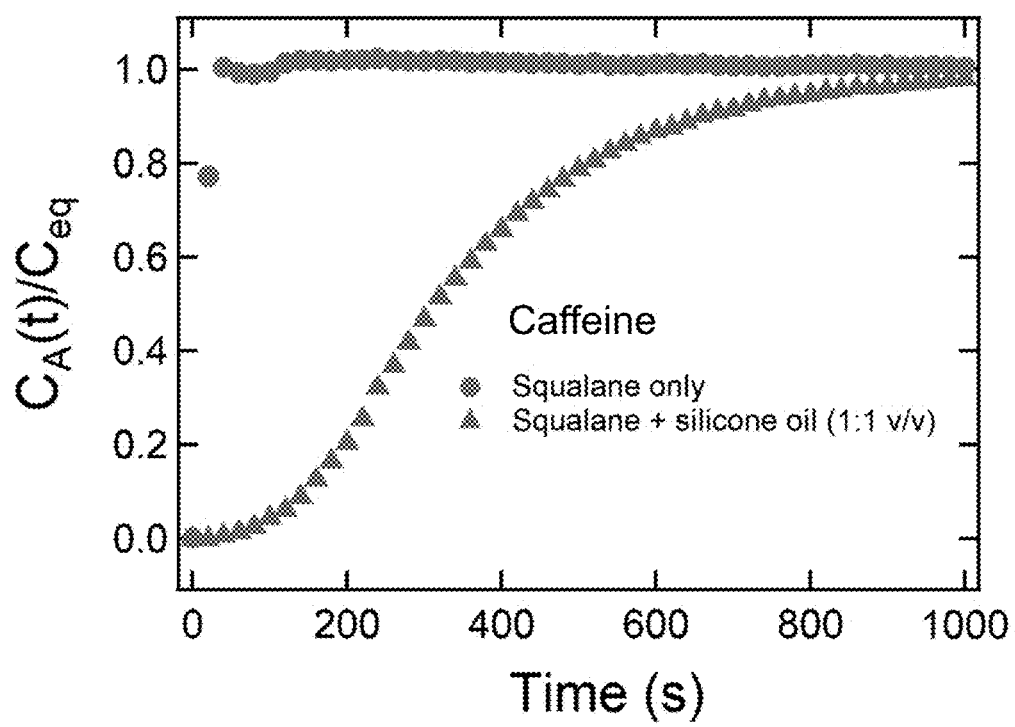

MULTI-PHASE LIQUID COMPOSITION, DEVICE FOR MEASURING PERMEABILITY OF DRUGS, AND METHOD FOR MEASURING PERMEABILITY OF DRUGS

CROSS-REFERENCE TO RELATED APPLICATION

This application claims priority to and the benefit of Korean Patent Applications No. 10-2017-0182395, filed on Dec. 28, 2017, and No. 10-2018-0155497, filed on Dec. 5, 2018, the entire contents of which are incorporated herein by reference.

FIELD

The present invention relates to a multi-phase liquid composition, a device for measuring the permeability of drugs, and a method for measuring the permeability of drugs.

BACKGROUND

Transport through a cell membrane plays an important role in many physiological phenomena. Various phenomena such as absorption of nutrients into cells, excretion of metabolic byproducts out of the cells, regulation of an ion concentration gradient to maintain proper membrane potential, and intercellular signaling are closely related to transport through cell membranes.

Development of new drugs is a representative field that considers transport through cell membranes to be important. Most drugs are administered orally, in which case absorption in the small intestine occurs. In order for the administered drug to transport to a desired tissue in the bloodstream and exhibit the intended effects, absorption in the small intestine must always come first. Therefore, it is critical to ensure the cell membrane permeability of new drug candidates to some degree in order to proceed to the next stage of development. In the pharmaceutical field, various assays are used to predict the cell membrane permeability of new drug candidates.

Two representative analysis methods are Caco-2 Assay and Parallel Artificial Membrane Permeability Assay (PAMPA). In both methods, the basic approaches are the same. They allow the drug to transport from the cell membrane outside (donor) to the inside for a certain period of time at the boundary of an actual cell membrane or an artificial cell membrane. Subsequently, the drug concentration of the portion corresponding to the cell membrane inside (acceptor) is obtained by HPLC or UV spectroscopy, from which the membrane permeability of the corresponding drugs is calculated. Since Caco-2 assays use actual cells, it can reflect all the effects of passive transport that occurs by the concentration gradient without using another energy source, and active transport that occurs with consumption of energy.

However, these are mainly used at the later stage of new drug development which requires more accurate information because of the time and cost required to culture cells. Meanwhile, PAMPA is a method of using artificial cell membranes instead of using actual cells. Artificial cell membranes are made by reapplying a solution in which a lipid is dissolved to a porous filter. Because PAMPA uses artificial cell membranes, it has the advantage of greatly reducing time and cost. Therefore, it is mainly used at the early stage of new drug development which requires rapid selection of a large number of new drug candidates.

PATENT LITERATURE (Patent Literature 1) Korean Patent No. 10-1568565
(Patent Literature 2) Korean Patent No. 10-1586036

SUMMARY

It is an object of the present invention to provide a multi-phase liquid composition which includes a lipid bilayer having characteristics similar to actual cell membranes, and can more easily and accurately measure the transport of drugs and the transport speed thereof through various methods such as UV spectroscopy or concentration confirmation.

There is provided a multi-phase liquid composition comprising: a first aqueous phase containing water or an aqueous solution; a second aqueous phase containing water or an aqueous solution; a lipid bilayer existing between the first aqueous phase and the second aqueous phase; and an organic phase making contact with a part or all of at least one of the first aqueous phase and the second aqueous phase, wherein the second aqueous phase includes two or more mixtures selected from the group consisting of squalene, silicone oil, squalane, and an alkane having 10 to 20 carbon atoms The first aqueous phase and the second aqueous phase have one surface so as to face each other on the basis of the lipid bilayer, and the lipid bilayer has a length of 0.5 mm or more with respect to the horizontal direction of one surface of each of the first aqueous phase and the second aqueous phase.

The lipid bilayer has a length of 0.5 mm to 10 mm with respect to the horizontal direction of one surface of each of the first aqueous phase and the second aqueous phase.

The multi-phase liquid composition has a structure in which the first aqueous phase, the lipid double layer, and the second aqueous phase are sequentially laminated.

The first aqueous phase is located at the bottommost part among the first aqueous phase, the lipid bilayer, and the second aqueous phase, and the first aqueous phase has a height of 1 μm or more in the direction perpendicular to the surface of the first aqueous phase.

The organic phase is located on the upper surface of the second aqueous phase, or the organic phase is located so as to surround the entirety of the second aqueous phase.

The organic phase is located so as to surround the lipid bilayer and the second aqueous phase, or the organic phase is located so as to surround the first aqueous phase, the lipid bilayer, and the second aqueous phase.

The organic phase is a complex organic phase containing squalane and silicone oil.

The organic phase is a complex organic phase in which squalane and silicone oil are mixed in a volume ratio of 0.2:1 to 9:1.

The multi-phase liquid composition further comprises a drug existing in the second aqueous phase.

It is another object of the present invention to provide a device for measuring the permeability of drugs including the multi-phase liquid composition.

There is provided a device for measuring the permeability of drugs comprising the multi-phase liquid composition.

The device for measuring the permeability of drugs further includes: a drug injection unit; an ultraviolet irradiation unit for irradiating ultraviolet rays to the multi-phase liquid composition; and an ultraviolet absorbance measuring unit for specifying ultraviolet absorbance of the multi-phase liquid composition.

The device for measuring the permeability of drugs further comprises a transparent container at which the multi-phase liquid composition is located.

It is a further object of the present invention to provide a method for measuring the permeability of drugs, which includes a lipid bilayer having characteristics similar to actual cell membranes, and can more easily and accurately measure the transport of drugs and the transport speed thereof through various methods such as UV spectroscopy or concentration confirmation.

There is provided a method for measuring the permeability of drugs comprising the steps of: injecting an organic phase in which a lipid is dissolved into a first aqueous phase containing water or an aqueous solution; injecting a second aqueous phase containing a drug and water or an aqueous solution into the organic phase to form a lipid bilayer; and measuring the time when the drug passes through the lipid bilayer.

There is also provided a method for measuring the permeability of drugs comprising the steps of: injecting an organic phase in which a lipid is dissolved into a first aqueous phase containing water or an aqueous solution; injecting a second aqueous phase containing water or an aqueous solution into the organic phase to form a lipid bilayer; injecting a drug into a second aqueous phase; and measuring the time when the drug passes through the lipid bilayer.

The step of measuring the time when a drug passes through the lipid bilayer includes a step of irradiating the ultraviolet rays having a wavelength that is absorbed by the drug to the first aqueous phase and measuring the absorbance to determine the permeation time and the permeation rate of the drug; or confirming the point of time when the concentration of the drug becomes the same at the first aqueous phase and the second aqueous phase to determine the permeation time and the permeation rate of the drug.

The organic phase includes a mixture of two or more selected from the group consisting of squalene, silicone oil, squalane, and an alkane having 10 to 20 carbon atoms.

The organic phase is a complex organic phase containing squalane and silicone oil.

The organic phase is a complex organic phase in which squalane and silicone oil are mixed in a volume ratio of 0.2:1 to 9:1.

DRAWINGS

FIG. 1 schematically illustrates a multi-phase liquid composition formed in examples and a method for measuring the permeability of drugs using the same.

FIG. 2 schematically illustrates a device for measuring the permeability of drugs used in the examples.

FIG. 3 illustrates changes in concentration according to the drug as determined in an experimental example.

FIG. 4 illustrates the results of measuring the permeability of caffeine using the multi-phase liquid compositions of the examples and comparative examples.

DETAILED DESCRIPTION

There is provided a multi-phase liquid composition including: a first aqueous phase containing water or an aqueous solution; a second aqueous phase containing water or an aqueous solution; a lipid bilayer existing between the first aqueous phase and the second aqueous phase; and an organic phase making contact with a part or all of at least one of the first aqueous phase and the second aqueous phase.

In addition, there is also provided a method for measuring the permeability of drugs including the multi-phase liquid composition.

Further, there is also provided a method for measuring the permeability of drugs including the steps of: injecting an organic phase in which a lipid is dissolved, into a first aqueous phase containing water or an aqueous solution; injecting a second aqueous phase containing a drug and water or an aqueous solution into the organic phase to form a lipid bilayer; and measuring the time when the drug passes through the lipid bilayer.

Further, there is also provided a method for measuring the permeability of drugs including the steps of: injecting an organic phase in which a lipid is dissolved, into a first aqueous phase containing water or an aqueous solution; injecting a second aqueous phase containing water or an aqueous solution into the organic phase to form a lipid bilayer; injecting a drug into the second aqueous phase; and measuring the time when the drug passes through the lipid bilayer.

Hereinafter, a multi-phase liquid composition, a device for measuring the permeability of drugs, and a method for measuring the permeability of drugs according to specific embodiments of the present invention will be described in detail.

As described above, according to one embodiment of the invention, a multi-phase liquid composition which includes a lipid bilayer having characteristics similar to actual cell membranes, and can more easily and accurately measure the transport of drugs and the transport speed thereof through various methods such as UV spectroscopy or concentration confirmation, can be provided.

The present inventors have actually implemented a multi-phase liquid composition having the above-mentioned specific composition and structure through a method of measuring the permeability of drugs to be described hereinafter, and found through experiments that the lipid bilayer existing in the multi-phase liquid composition can have characteristics that are more similar to actual cell membranes as compared with the lipid bilayer provided by previously known methods, and that due to the existence of respective phases contained in the multi-phase liquid composition, the transport of drugs and the transport speed thereof can be more easily and accurately measured through various methods such as UV spectroscopy or concentration confirmation.

More specifically, the multi-phase liquid composition of the embodiment may include: a first aqueous phase containing water or an aqueous solution; a second aqueous phase containing water or an aqueous solution; and a lipid bilayer existing between the first aqueous phase and the second aqueous phase, and the organic phase may make contact with a part or all of at least one of the first aqueous phase and the second aqueous phase.

The multi-phase liquid composition of this embodiment is implemented through a method of measuring the permeability of drugs to be described hereinafter, and in particular, the lipid bilayer existing between the first aqueous phase and the second aqueous phase can be formed through the steps of: injecting an organic phase in which a lipid is dissolved, into a first aqueous phase containing water or an aqueous solution; and injecting a second aqueous phase containing a drug and water or an aqueous solution into the organic phase to form a lipid bilayer.

As the multi-phase liquid composition of the embodiment includes the first aqueous phase, the second aqueous phase, the lipid bilayer, and the organic phase as described above, it can have a considerably stable structure, and thereby, can be easily used for measurement of the permeability or the permeation rate of drugs.

In the multi-phase liquid composition of this embodiment, the first aqueous phase and the second aqueous phase may have one surface so as to face each other on the basis of the lipid bilayer, and the lipid bilayer may have a length of 0.5 mm or more or 0.5 mm to 10 mm with respect to the horizontal direction of one surface of each of the first aqueous phase and the second aqueous phase.

If the length of the lipid bilayer is too short with respect to the horizontal direction of one surface of each of the first aqueous phase and the second aqueous phase, measurement of the permeability or permeation rate of drugs may not be easy, and it may cause a problem that a measurable minimum level cannot be reached due to a small amount of drug permeation.

The specific distribution within the multi-phase liquid composition of the embodiment is not particularly limited, but as a specific example, the multi-phase liquid composition of the embodiment may have a structure in which the first aqueous phase, the lipid bilayer, and the second aqueous phase are sequentially laminated.

In addition, when the multi-phase liquid composition of the embodiment has a structure in which the first aqueous phase, the lipid bilayer, and the second aqueous phase are sequentially laminated, the first aqueous phase may be located at the bottommost part among the first aqueous phase, the lipid bilayer, and the second aqueous phase.

The height of the first aqueous phase in the direction perpendicular to the surface thereof is not particularly limited, but in order to facilitate the measurement of the permeability of drugs and the like, it may have a height of 1 μm or more.

Meanwhile, as described above, the organic phase may make contact with a part or all of at least one of the first aqueous phase and the second aqueous phase, and more specifically, the organic phase may be located on the upper surface of the second aqueous phase, or the organic phase may be located so as to surround the entirety of the second aqueous phase.

When the multi-phase liquid composition of the embodiment has a structure in which the first aqueous phase, the lipid bilayer, and the second aqueous phase are sequentially laminated, the organic phase may be located so as to surround the lipid bilayer and the second aqueous phase, or the organic phase may be located so as to surround the first aqueous phase, the lipid bilayer, and the second aqueous phase.

The first aqueous phase and the second aqueous phase may be water or an aqueous solution. The type of the aqueous solution is not particularly limited, and it may include various drugs and organic solvent components such as ethanol, methanol, and dimethyl sulfoxide (DMSO).

The type of lipid constituting the lipid bilayer is not particularly limited, but it may be a phospholipid.

Specific examples of the lipid may be phosphatidylcholines (PC) including 1,2-dioleoyl-sn-glycero-3-phosphocholine (DOPC), 1-palmitoyl-2-oleoyl-sn-glycero-3-phosphocholine (POPC), or the like; phosphatidylglycerols (PG) including 1,2-dioleoyl-sn-glycero-3-phosphoglycerol (DOPE), and the like, phosphatidylserines (PS) including 1-palimitoyl-2-oleoyl-sn-glycero-3-phosphoserine (POPS), and a cholesterol, or a mixture of two or more thereof.

The type of the organic phase may be, for example, squalene, silicone oil, squalane, an alkane having 10 to 20 carbon atoms such as hexadecane or dodecane, and preferably, a mixture of two or more of the above-mentioned organic phases can be used.

The silicone oil may have viscosity of 1 to 100 mPa·s at room temperature.

More preferably, the organic phase is a complex organic phase in which squalane and silicone oil are mixed, or a complex organic phase in which squalane and silicone oil are mixed in a volume ratio of 0.2:1 to 9:1 or a volume ratio of 0.5:1 to 2:1.

Such a composite organic phase in which squalane and silicone oil are mixed may have the advantage of increasing the stability of the lipid bilayer surrounded by the complex organic phase.

Specifically, the squalane is not easily oxidized and can have characteristics having affinity with lipids, and can serve as a solvent for dissolving lipids in the complex organic phase and uniformly dispersing the lipids.

The silicone oil has a certain degree of high viscosity, and can act as a bad solvent for lipids in the complex organic phase to promote the spontaneous adhesion of two different lipid monolayers.

In addition, the complex organic phase in which squalane and silicone oil are mixed may have characteristics of partially inducing interaction between lipid monolayers while uniformly dispersing lipids as a whole in addition to the characteristics of each of squalane and silicone oil. Accordingly, the stability of the lipid bilayer can be further increased as compared with the case where one kind of organic solvent is used alone.

Meanwhile, as described above, as the organic phase, a complex organic phase obtained by mixing squalane and silicone oil in a volume ratio of 0.2:1 to 9:1 or a volume ratio of 0.5:1 to 2:1 may be used.

In this case, when the proportion of any one of squalane and silicone oil in the complex organic phase become excessively large, it is difficult for spontaneous attachment of lipid monolayers to occur, or lipid solubility may be greatly reduced.

The multi-phase liquid composition may further include a drug existing in the second aqueous phase.

When a drug is injected into the second aqueous phase of the multi-phase liquid composition, a concentration gradient of drugs exists between the second aqueous phase and the first aqueous phase, and therefore the drug transports through the lipid bilayer.

Consequently, by using such characteristics of the multi-phase liquid composition, it is possible to more easily and accurately confirm the permeation time or permeation rate of the drug through the lipid bilayer.

Further, as described hereinafter, in the process of forming the multi-phase liquid composition, an organic phase in which lipid is dissolved is injected into a first aqueous phase containing water or an aqueous solution. When a lipid bilayer is formed by injecting a second aqueous phase containing a drug and water or an aqueous solution into the organic phase, a first aqueous phase containing a drug is located on the lipid bilayer.

Then, after a predetermined period of time, the drug is transported through the lipid bilayer due to the concentration gradient of drugs between the second aqueous phase and the first aqueous phase.

Meanwhile, according to another embodiment of the present invention, a device for measuring the permeability of drugs including the multi-phase liquid composition can be provided.

As described above, the multi-phase liquid composition may have characteristics that are more similar to actual cell membranes as compared with the lipid bilayer provided by previously known methods, and the transport time and the transport speed of drugs can be more easily and accurately measured through various methods such as UV spectroscopy or concentration confirmation due to the existence of respective phases in the multi-phase liquid composition.

Consequently, by using the device for measuring the permeability of drugs containing the multi-phase liquid composition, the transport time and the transport speed of drugs can be measured more easily and accurately.

More specifically, after injecting drugs or injecting drugs in the process of preparing the multi-phase liquid composition, or injecting drugs in a state where the multi-phase liquid composition is formed, the time when the drug passes through the lipid bilayer is confirmed, thereby confirming the transport time and transport speed of drugs through the cell membrane.

In the device for measuring the permeability of drugs of the above embodiment, the method for measuring the transport time and the transport speed of drugs is not particularly limited, but specifically, ultraviolet rays of a wavelength that is absorbed by the drug may be irradiated to the first aqueous phase, and the absorbance may be measured to determine the permeation time and the permeation rate of drugs, or alternatively, the permeation time and the permeation rate of drugs may be determined by confirming the point of time when the concentration of the drug becomes the same in the first aqueous phase and the second aqueous phase.

The device for measuring the permeability of drugs of the embodiment may further include various additional detailed configurations in addition to the configuration including the multi-phase liquid composition.

For example, the device for measuring the permeability of drugs may further include: a drug injection unit; an ultraviolet irradiation unit for irradiating ultraviolet rays to the multi-phase liquid composition; and an ultraviolet absorbance measuring unit for specifying ultraviolet absorbance of the multi-phase liquid composition.

Specific configurations of the drug injection unit, the ultraviolet ray irradiation unit, and the ultraviolet absorbance measuring unit or the type of the device are not particularly limited, and various devices known to satisfy the above functions can be used without particular limitation.

The drug injection unit may act to inject drugs into the multi-phase liquid composition, and in order to form the multi-phase liquid composition in the device for measuring the permeability of drugs, it may also serve to inject a second aqueous phase containing a drug and water or an aqueous solution as described above.

In the device for measuring the permeability of drugs of the above embodiment, in order to confirm the point of time when the concentrations of the drug in the first aqueous phase and the second aqueous phase become the same, it may include various measuring devices, for example, an ultraviolet absorbance measuring unit, and the like.

The device for measuring the permeability of the drug may further include a transparent container at which the multi-phase liquid composition is located.

By using the transparent container, measurement of the ultraviolet absorbance or confirmation of the concentration may be easier.

The contents of the multi-phase liquid composition and the detailed components contained therein contain all of those described above.

According to another embodiment of the invention, a method for measuring the permeability of drugs can be provided, including the steps of: injecting an organic phase in which lipid is dissolved, into a first aqueous phase containing water or an aqueous solution; injecting a second aqueous phase containing a drug and water or an aqueous solution into the organic phase to form a lipid bilayer; and measuring the time when the drug passes through the lipid bilayer.

The multi-phase liquid composition of the above-described embodiment can be formed through the steps of injecting an organic phase in which a lipid is dissolved, into a first aqueous phase containing water or an aqueous solution, and injecting a second aqueous phase containing a drug and water or an aqueous solution into the organic phase to form a lipid bilayer.

The permeation time and permeation rate of drugs can be determined by measuring the time when the drug passes through the lipid bilayer in the formed multi-phase liquid composition.

As described above, the multi-phase liquid composition to be formed may have characteristics that are more similar to actual cell membranes as compared with the lipid bilayer provided by previously known methods, and, due to the existence of respective phases in the multi-phase liquid composition, the transport time and the transport speed of the drug can be more easily and accurately measured through various methods such as UV spectroscopy or concentration confirmation.

Specifically, through the step of injecting an organic phase in which a lipid is dissolved, into a first aqueous phase containing water or an aqueous solution, lipid molecules spontaneously form a lipid monolayer at the interface between the first aqueous phase and the organic phase.

Then, when the second aqueous phase containing a drug and water or an aqueous solution is injected into the organic phase, a lipid monolayer is formed even at the interface between the second aqueous phase and the organic phase. When the two lipid monolayers meet while coming close to each other after a certain period of time, they can spontaneously adhere to each other to form a lipid bilayer.

Herein, during observation with fluorescence microscopy, it can be clearly seen that the lipid bilayer is formed, and the organic phase existing between the two lipid monolayers escapes, so it can be confirmed that a lipid bilayer is formed.

In the process of forming the multi-phase liquid composition, when an organic phase in which lipid is dissolved is injected into a first aqueous phase containing water or an aqueous solution, and a second aqueous phase containing a drug and water or an aqueous solution is injected into the organic phase to form a lipid bilayer, the first aqueous phase containing the drug is positioned on the lipid bilayer.

Then, after a predetermined time, due to the concentration gradient of drugs between the second aqueous phase and the first aqueous phase, the drug existing in the second aqueous phase passes through the lipid bilayer and transports to the first aqueous phase.

Meanwhile, according to another embodiment of the present invention, a method for measuring the permeability of drugs can be provided, including the steps of: injecting an organic phase in which a lipid is dissolved, into a first aqueous phase containing water or an aqueous solution; injecting a second aqueous phase containing water or an aqueous solution into the organic phase to form a lipid bilayer; and measuring the time when the drug passes through the lipid bilayer.

A multi-phase liquid composition of one embodiment described above can be formed through the steps of injecting an organic phase in which a lipid is dissolved, into a first aqueous phase containing water or an aqueous solution, and injecting a second aqueous phase containing water or an aqueous solution into the organic phase to form a lipid bilayer.

The permeation time and permeation rate of drugs can be determined by measuring the time when a drug is injected in the second aqueous phase in the formed multi-phase liquid composition and the drug passes through the lipid bilayer.

As described above, the formed multi-phase liquid composition may have characteristics that are more similar to actual cell membranes as compared with the lipid bilayer provided by previously known methods, and, due to the existence of phases in the multi-phase liquid composition, the transport time and the transport speed of drugs can be more easily and accurately measured through various methods such as UV spectroscopy or concentration confirmation.

Specifically, through the step of injecting an organic phase in which a lipid is dissolved, into a first aqueous phase containing water or an aqueous solution, lipid molecules spontaneously form a lipid monolayer at the interface between the first aqueous phase and the organic phase.

Then, when the second aqueous phase containing water or an aqueous solution is injected into the organic phase, a lipid monolayer is formed even at the interface between the second aqueous phase and the organic phase. When the two lipid monolayers formed meet while coming close to each other after a certain period of time, they can spontaneously adhere to each other to form a lipid bilayer.

Herein, during observation through fluorescence microscopy, it can be clearly seen that the lipid bilayer is formed, and the organic phase existing between the two lipid monolayers escapes, so it can be confirmed that a lipid bilayer is formed.

When a drug is injected into the first aqueous phase of the multi-phase liquid composition, a concentration gradient of drugs exists between the second aqueous phase and the first aqueous phase, and therefore the drug passes through the lipid bilayer and transports to the second aqueous phase.

Consequently, by using such a characteristic of the multi-phase liquid composition, it is possible to more easily and accurately confirm the permeation time or permeation rate of the drug through the lipid bilayer.

Meanwhile, in the method for measuring the permeability of drugs of the above-described embodiments, various devices and methods may be used in the step of measuring the time when the drug passes through the lipid bilayer. For example, the method may include a step of irradiating the ultraviolet rays having a wavelength that is absorbed by the drug to the first aqueous phase and measuring the absorbance to determine the permeation time and the permeation rate of drugs, or confirming the point of time when the concentration of drugs becomes the same at the first aqueous phase and the second aqueous phase to determine the permeation time and the permeation rate of drugs.

More specifically, when the lipid bilayer is formed, a concentration gradient of drugs exists between the second aqueous phase and the first aqueous phase, and therefore the drug passes through the lipid bilayer and transports down (in the direction from the second aqueous phase to the first aqueous phase). As a result, by continuously irradiating the ultraviolet rays of the wavelength that is absorbed by the drug, the absorbance of the drug in the lower part over time is measured in real time, or the time taken until the concentration gradient of the drug disappears between the second aqueous phase and the first aqueous phase is confirmed, thereby confirming the permeation time or the permeation rate of the drug.

The measurement object of the permeation time or permeation rate of the cell membrane is not limited to specific types of drugs.

For example, as various drugs, various anti-cancer drugs, gene drugs, or the like can be used, and the permeation time or the permeation rate can be measured for various drugs such as hydrophilic drugs including caffeine, acetaminophen, antipyrine, or the like, and lipophilic drugs including carbamazepine, coumarin, or the like.

As described above, the first aqueous phase and the second aqueous phase may be water or an aqueous solution, and the type of the aqueous solution is not particularly limited, but it may include various drugs and solvent components such as ethanol, methanol, and dimethyl sulfoxide (DMSO).

The type of lipid constituting the lipid bilayer is not particularly limited, but it may be a phospholipid.

Specific examples of the lipid may be phosphatidylcholines (PC) including 1,2-dioleoyl-sn-glycero-3-phosphocholine (DOPC), 1-palmitoyl-2-oleoyl-sn-glycero-3-phosphocholine (POPC), and the like; phosphatidylglycerols (PG) including 1,2-dioleoyl-sn-glycero-3-phosphoglycerol (DOPG), and the like, phosphatidylserines (PS) including 1-palmitoyl-2-oleoyl-sn-glycero-3-phosphoserine (POPS), and a cholesterol, or a mixture of two or more thereof.

The type of the organic phase is not particularly limited, and for example, it may be squalene, silicone oil, squalane, an alkane having 10 to 20 carbon atoms such as hexadecane or dodecane, and preferably, a mixture of two or more of the above-mentioned organic phases can be used.

The silicone oil may have a viscosity of 1 to 100 mPa·s at room temperature.

More preferably, the organic phase is a complex organic phase in which squalane and silicone oil are mixed in a volume ratio of 0.5:1 to 2:1.

According to the present invention, a multi-phase liquid composition which includes a lipid bilayer having characteristics that are similar to actual cell membranes, and can more easily and accurately measure the transport of drugs and the transport speed thereof though various methods such as UV spectroscopy or concentration confirmation, a device for measuring the permeability of drugs including the multi-phase liquid composition, and a method for measuring the permeability of drugs, which includes a lipid bilayer having characteristics that are similar to actual cell membranes, and which can more easily and accurately measure the transport of drugs and the transport speed thereof through various methods such as UV spectroscopy or concentration confirmation, can be provided.

The invention will be described in more detail by way of the following examples. However, the following examples are given for illustrative purposes only, and the scope of the present invention is not intended to be limited by the following examples.

Example: Formation of Multi-Phase Liquid Composition and Method for Measuring the Permeability of Drugs A DOPC lipid dissolved in chloroform and commercially available was collected in a glass vial, and chloroform was removed by blowing nitrogen.

The lipid film was left in the glass vial, to which the organic phase (1:1 (v/v) mixture of squalane and silicone oil (AR20)) was added, and then sonication was performed for 10-15 minutes to uniformly disperse the lipid in the oil.

Finally, an oil solution in which the lipid was dissolved (DOPC concentration: 4 mg/ml) was obtained.

Then, distilled water was added to a UV cuvette and the prepared lipid solution was added thereon.

It was confirmed that lipid molecules spontaneously formed a lipid monolayer at the water/oil interface.

Then, an aqueous solution droplet (1 μl) in which the drug to be measured was dissolved was injected into the oil layer of the cuvette, and it was confirmed that a lipid monolayer was formed even at the interface between an aqueous droplet and the oil.

When the two lipid monolayers formed met while coming close to each other after a certain period of time passed, it was confirmed that they spontaneously adhered to each other to form a lipid bilayer.

At this time, the process of producing the lipid bilayer was performed by adding a small amount of fluorescently labeled lipid and observing it through a fluorescence microscope. Under observation by fluorescence microscopy, it was clearly seen that while a lipid bilayer was formed, the oil existing between the two lipid monolayers escaped. It was concluded from this that the lipid bilayer was formed.

A schematic diagram of the multi-phase liquid composition thus formed and the method for measuring the permeability of drugs using the same is shown in FIG. 1.

Comparative Example

An oil solution in which a lipid (DOPC concentration: 4 mg/ml) was dissolved was obtained in the same manner as in Example 1, except that squalane was used alone instead of the "organic phase (1:1(v/v) mixture of squalane and silicone oil (AR20))".

Thereafter, a lipid monolayer was prepared in the same manner as in Example 1, and an aqueous solution droplet (1 μl) in which the drug to be measured was dissolved was injected into the oil layer of the cuvette.

At this time, it was confirmed that the aqueous solution droplets burst soon after the aqueous solution droplet was injected, instead of forming a lipid bilayer in such a way that the two lipid monolayers come close and spontaneously adhered to each other When the aqueous solution droplets burst, the change in concentration of the drug over time suddenly rises to an equilibrium value at some point, and these contents are confirmed in FIG. 4.

When squalane alone was used as an organic phase instead of a mixture of squalane and silicone oil, it was confirmed that the entire system was unstable so as to burst the aqueous solution droplet before the formation of the lipid bilayer.

Experimental Example: Real-Time Observation of Lipid Bilayer Permeation by Drug (1) Measurement Method When a lipid bilayer is formed, the drug transports down through the lipid bilayer because a concentration gradient of the drug exists between the aqueous solution droplet and the lower water layer.

If the ultraviolet rays of the wavelength that is absorbed by the drug are continuously irradiated to the water layer under a cuvette, the absorbance of the lower portion of drugs over time can be measured in real time.

At this time, a magnetic stirring bar is placed under the UV cuvette and the lower water layer is continuously stirred during the measurement. This makes it unnecessary to consider the time when the drug passes through the lipid bilayer and diffuses to the area irradiated with UV. The results of the UV absorbance over time reflect only the pure permeation of drugs through the lipid bilayer.

The device for measuring the permeability of drugs to which such a method is applied is schematically illustrated in FIG. 2.

Further, it was confirmed that the concentration of aqueous solution and the UV absorbance of each drug had a linear relationship before the experiment of the lipid bilayer permeation.

The R2 value was calculated in order to determine how well the concentration and absorbance correlate at each wavelength, and the wavelength at which this value exceeds 0.99 was irradiated in the experiment.

Therefore, from the absorbance data obtained in real time, the drug concentration in the lower part was directly obtained, thereby calculating the lipid bilayer permeability of the drug.

(2) Measurement Result

FIG. 3 is a graph showing changes in concentrations of five drugs.

More specifically, in FIG. 3, $C_A(t)$ means the concentration of an acceptor solution over time (where the first aqueous phase is located under the cuvette, where the drug reaches through the first lipid bilayer) and $C_{eq}$ means the equilibrium concentration of the acceptor solution droplet (serving as a donor solution to provide a drug), and the acceptor solution, and is calculated by the following General Formula 1.

$$C_{eq}=C_D(0)V_D/(V_D+V_A)$$ [General Formula 1]

In General Formula 1, $V_A$ and $V_D$ are respectively the volume of a first aqueous phase (acceptor) and the volume of a second aqueous phase (donor, droplet), and $C_D(0)$ represents the drug concentration of the initial aqueous solution droplet.

Table 1 below shows the permeability confirmed for five drugs by using the method of the example and PAMPA, respectively.

TABLE 1

| Compound | Permeability according to PAMA ($10^{-6}$ cm/s) | Permeability according to examples ($10^{-6}$ cm/s) |
|---|---|---|
| Caffeine | 9.89 | 248.1 |
| Theophylline | 3.53 | 226.5 |
| Antipyrine | 7.51 | 200.0 |
| Acetaminophen | 3.5 | 113.1 |
| Cimetidine | 0 | 7.2 |

As can be seen in FIG. 3 and Table 1 above, it is clear that each drug has different permeability to the lipid bilayer.

Another noteworthy point is that, except for the drug (cimetidine) having very low permeability, most of the drugs used in the experiment reached equilibrium concentrations in less than 1 hour.

Considering that it requires a time of at least about 4 to 5 hours even in methods such as a conventional PAMPA, it was confirmed that the lipid bilayer permeability of the drug can be measured more efficiently within a shorter time in the examples.

What is claimed is:

1. A multi-phase liquid composition comprising:
a first aqueous phase containing water or an aqueous solution; a second aqueous phase containing water or an aqueous solution; a lipid bilayer existing between the first aqueous phase and the second aqueous phase; and an organic phase making contact with a part or all of at least one of the first aqueous phase and the second aqueous phase,
wherein the organic phase includes two or more mixtures selected from the group consisting of squalene, silicone oil, squalane and an alkane having 10 to 20 carbon atoms,
wherein the lipid bilayer is formed by contacting a first lipid monolayer that partially covers the surface of the first aqueous phase, and a second lipid monolayer that fully covers the second aqueous phase,
wherein the lipid bilayer has a length of 0.5 mm or more.

2. The multi-phase liquid composition of claim 1, wherein the first aqueous phase and the second aqueous phase have one surface so as to face each other on the basis of the lipid bilayer.

3. The multi-phase liquid composition of claim 1, wherein it has a structure in which the first aqueous phase, the lipid double layer, and the second aqueous phase are sequentially laminated.

4. The multi-phase liquid composition of claim 3, wherein the first aqueous phase is located at the bottommost part among the first aqueous phase, the lipid bilayer, and the second aqueous phase, and the first aqueous phase has a height of 1 μm or more in the direction perpendicular to the surface of the first aqueous phase.

5. The multi-phase liquid composition of claim 1, wherein the organic phase is located on the upper surface of the second aqueous phase, or the organic phase is located so as to surround the entirety of the second aqueous phase.

6. The multi-phase liquid composition of claim 3, wherein the organic phase is located so as to surround the lipid bilayer and the second aqueous phase, or the organic phase is located so as to surround the first aqueous phase, the lipid bilayer, and the second aqueous phase.

7. The multi-phase liquid composition of claim 1, wherein the organic phase is a complex organic phase in which squalane and silicone oil are mixed in a volume ratio of 0.2:1 to 9:1.

8. The multi-phase liquid composition of claim 1, further comprising a drug existing in the second aqueous phase.

9. A method for measuring the permeability of drugs comprising the steps of:
injecting an organic phase in which a lipid is dissolved into a first aqueous phase containing water or an aqueous solution;
injecting a second aqueous phase containing a drug and water or an aqueous solution into the organic phase to form a lipid bilayer; and
measuring the time when the drug passes through the lipid bilayer.

10. A method for measuring the permeability of drugs comprising the steps of:
injecting an organic phase in which a lipid is dissolved into a first aqueous phase containing water or an aqueous solution;
injecting a second aqueous phase containing water or an aqueous solution into the organic phase to form a lipid bilayer;
injecting a drug into a second aqueous phase; and
measuring the time when the drug passes through the lipid bilayer.

11. The method for measuring the permeability of drugs of claim 9, wherein the step of measuring the time when a drug passes through the lipid bilayer includes a step of irradiating the ultraviolet rays having a wavelength that is absorbed by the drug to the first aqueous phase and measuring the absorbance to determine the permeation time and the permeation rate of the drug; or
confirming the point of time when the concentration of the drug becomes the same at the first aqueous phase and the second aqueous phase to determine the permeation time and the permeation rate of the drug.

12. The method for measuring the permeability of drugs of claim 9, wherein
the organic phase includes a mixture of two or more selected from the group consisting of squalene, silicone oil, squalane, and an alkane having 10 to 20 carbon atoms.

13. The method for measuring the permeability of drugs of claim 9, wherein
the organic phase is a complex organic phase containing squalane and silicone oil.

14. The multi-phase liquid composition of claim 9, wherein the organic phase is a complex organic phase in which squalane and silicone oil are mixed in a volume ratio of 0.2:1 to 9:1.

15. The method for measuring the permeability of drugs of claim 10, wherein
the step of measuring the time when a drug passes through the lipid bilayer includes a step of irradiating the ultraviolet rays having a wavelength that is absorbed by the drug to the first aqueous phase and measuring the absorbance to determine the permeation time and the permeation rate of the drug; or
confirming the point of time when the concentration of the drug becomes the same at the first aqueous phase and the second aqueous phase to determine the permeation time and the permeation rate of the drug.

16. The method for measuring the permeability of drugs of claim 10, wherein
the organic phase includes a mixture of two or more selected from the group consisting of squalene, silicone oil, squalane, and an alkane having 10 to 20 carbon atoms.

17. The method for measuring the permeability of drugs of claim 10, wherein
the organic phase is a complex organic phase containing squalane and silicone oil.

18. The method of measuring the permeability of drugs of claim 10, wherein the organic phase is a complex organic phase in which squalane and silicone oil are mixed in a volume ratio of 0.2:1 to 9:1.

19. The multi-phase liquid composition of claim 1, wherein the lipid bilayer has a length of 0.5 mm to 10 mm.

* * * * *